United States Patent
Burgfels et al.

(10) Patent No.: US 10,252,250 B2
(45) Date of Patent: Apr. 9, 2019

(54) PROCESS OF PRODUCING ZEOLITE-BASED CATALYSTS FOR CONVERTING OXYGENATES TO LOWER OLEFINS

(76) Inventors: Gotz Burgfels, Bad Aibling (DE); Manfred Frauenrath, Grosskarolinenfeld (DE); Sven Pohl, Frankfurt am Main (DE); Martin Rothamel, Frankfurt am Main (DE); Stephane Haag, Frankfurt am Main (DE)

( * ) Notice: Subject to any disclaimer, the term of this patent is extended or adjusted under 35 U.S.C. 154(b) by 408 days.

(21) Appl. No.: 13/809,938

(22) PCT Filed: Jul. 8, 2011

(86) PCT No.: PCT/EP2011/061679
§ 371 (c)(1),
(2), (4) Date: Mar. 7, 2013

(87) PCT Pub. No.: WO2012/007398
PCT Pub. Date: Jan. 19, 2012

(65) Prior Publication Data
US 2013/0156688 A1 Jun. 20, 2013

(30) Foreign Application Priority Data
Jul. 12, 2010 (DE) .......... 10 2010 026 880

(51) Int. Cl.
*B01J 29/06* (2006.01)
*B01J 29/40* (2006.01)
*B01J 35/02* (2006.01)
*B01J 21/04* (2006.01)
*B01J 37/00* (2006.01)
*B01J 37/04* (2006.01)
*B01J 37/06* (2006.01)
*B01J 37/30* (2006.01)
*C07C 1/20* (2006.01)

(52) U.S. Cl.
CPC ............... *B01J 29/40* (2013.01); *B01J 21/04* (2013.01); *B01J 35/02* (2013.01); *B01J 35/023* (2013.01); *B01J 37/0063* (2013.01); *B01J 37/04* (2013.01); *B01J 37/06* (2013.01); *B01J 37/30* (2013.01); *C07C 1/20* (2013.01); *B01J 2229/12* (2013.01); *B01J 2229/42* (2013.01); *C07C 2529/40* (2013.01); *Y02P 20/52* (2015.11)

(58) Field of Classification Search
CPC ........ B01J 29/40; B01J 35/02; B01J 354/023; B01J 37/0063; B01J 37/30; B01J 2229/40; B01J 2229/42; B01J 35/023
USPC .......................... 502/64, 68, 69, 70, 71, 77
See application file for complete search history.

(56) References Cited

U.S. PATENT DOCUMENTS

| | | | |
|---|---|---|---|
| 3,702,886 A | 11/1972 | Argauer et al. | |
| 3,926,782 A | 12/1975 | Plank et al. | |
| 4,025,572 A | 5/1977 | Lago | |
| 5,063,187 A | 11/1991 | Burgfels et al. | |
| 7,229,941 B2 | 6/2007 | Burgfels et al. | |
| 7,417,004 B2 | 8/2008 | Jun et al. | |
| 7,880,048 B2 | 2/2011 | Pigeat et al. | |
| 2003/0149322 A1 | 8/2003 | Koss et al. | |
| 2004/0138053 A1* | 7/2004 | Burgfels et al. | 502/64 |
| 2007/0149384 A1* | 6/2007 | Ghosh | B01J 29/40 502/60 |
| 2012/0253090 A1 | 10/2012 | Burgfels et al. | |

FOREIGN PATENT DOCUMENTS

| | | |
|---|---|---|
| DE | 251711 A1 | 11/1987 |
| DE | 10027159 A1 | 12/2001 |
| GB | 1601915 A | 11/1981 |
| WO | 2004030815 A1 | 4/2004 |

OTHER PUBLICATIONS

Kirk et al., "Catalysis," Kirk-Othmer Encyclopedia of Chemical Technology, 4th ed., vol. 5, p. 171, Dec. 1998.*
International Search Report, dated Sep. 26, 2011, with respect to International Application Serial No. PCT/EP/2011/061679.

* cited by examiner

*Primary Examiner* — Elizabeth D Wood

(57) ABSTRACT

A process of producing a catalyst based on pentasil-type crystalline aluminosilicate is described, including the steps of (a) treating hydrous aluminum oxide with an aqueous, acid-containing medium, (b) mixing the hydrous aluminum oxide treated with aqueous, acid-containing medium from step (a) with an H-zeolite and (c) calcining the mixture obtained in step (b). In addition, a catalyst is disclosed which is obtained by such a process, as well as its use in CMO and OTO processes.

14 Claims, No Drawings

PROCESS OF PRODUCING ZEOLITE-BASED CATALYSTS FOR CONVERTING OXYGENATES TO LOWER OLEFINS

The invention relates to a process of producing zeolite-based catalysts and the use of the catalysts in the conversion of oxygenates to lower olefins, in particular of methanol to propylene.

Catalysts based on crystalline aluminosilicates which are produced from an aluminium source, a silicon source, an alkali source, a template (e.g. a tetrapropylammonium compound) and water are known from U.S. Pat. No. 3,702,886.

DE-A-28 22 725 describes the production of methanol conversion catalysts based on crystalline aluminosilicates. The diameter of the primary crystallites is 1 µm and more. The production of primary crystallites with diameters far greater than 1 µm is intended. For this, crystal growth must be promoted by higher temperatures and nucleation inhibited by low concentrations of the templates essential for the crystallization of the zeolites. There is no mention of the use of binders or the size of the agglomerates.

According to DE-A-24 05 909 (FR-A-2 217 408), catalysts for converting hydrocarbons are produced on the basis of ZSM-5 type zeolites, wherein the average diameter of the primary crystallites is in the range of from 0.005 to 0.1 µm. Agglomerates of the order of from 0.1 to 1 µm are produced from the primary crystallites. To produce the catalysts, aluminium oxide i.a. is added, as binder, to the agglomerates, wherein other binders are, however, also specified as being of equal value. Nothing is said about the particle size of the binders. Furthermore, the synthesis was carried out in the presence of sulphuric acid and using $Al_2(SO_4)_3 \cdot xH_2O$.

U.S. Pat. No. 4,025,572 relates to a process for producing specific hydrocarbon mixtures, wherein the catalyst bed contains a zeolite, among other things. The synthesis of the zeolite is carried out in the presence of sulphuric acid and using $Al_2(SO_4)_3 \cdot xH_2O$. According to one example, the zeolite catalyst is mixed with 90 wt.-% aluminium oxide and pelletized.

EP 0 369 364 A1 describes catalysts based on pentasil-type crystalline aluminosilicates with an Si/Al atomic ratio of at least 10, which are constructed from primary crystallites with an average diameter of at least 0.1 µm and at most 0.9 µm. The size of the primary crystallites is regarded as important for the life of the catalysts. A methanol-to-olefin process and an olefin-to-diesel process are given as application examples.

European patent application EP 1 424 128 A1 discloses catalysts based on crystalline aluminosilicate, which have primary crystallites with an average diameter of at least 0.01 µm and less than 0.1 µm and a pore volume of from 0.3 to 0.8 cm³/g. These catalysts can be used in principle on a laboratory scale in the methanol-to-olefin process. However, they have the disadvantage that they have a comparatively low mechanical strength, in particular a lateral compressive strength of less than 0.8 kp/mm (7.8 N/mm). This can in particular lead to problems during transport, as well as during filling and operation of industrial reactors, as the catalysts can break up, which results in a comparatively short life.

The object of the invention, on the other hand, is to provide a process of producing catalysts based on crystalline, highly active aluminosilicates which display an optimum activity and improved stability and strength, and thus a very good life, in catalytic processes, in particular in methanol-to-propylene (MTP) conversion processes. This object is achieved by the process according to the invention and the catalysts that can be obtained with it.

The invention relates to a process of producing a catalyst based on pentasil-type crystalline aluminosilicate, comprising the steps of:
  (a) treating hydrous aluminium oxide with an aqueous, acid-containing medium,
  (b) mixing the hydrous aluminium oxide treated with aqueous, acid-containing medium from step (a) with an H-zeolite with an average diameter of the primary crystallites of between 0.01 µm and less than 0.1 µm and
  (c) calcining the mixture obtained in step (b),
  wherein at least 95 vol.-% of the particles of the hydrous aluminium oxide (relative to the average diameter) are smaller than or equal to 100 µm.

It was surprisingly found that the process according to the invention results in catalysts with increased life due to increased lateral compressive strength, as well as excellent selectivity and activity. By pre-mixing the hydrous aluminium oxide with the aqueous, acid-containing medium in step (a) of the process according to the invention, a significant improvement in the catalytic properties of the catalysts according to the invention is achieved, compared with catalysts which can be obtained by adding aqueous, acid-containing medium to a mixture of H-zeolite and hydrous aluminium oxide.

The hydrous aluminium oxide used in step (a) can be obtained for example by hydrolysis of aluminium organic compounds, such as e.g. aluminium trialkyls or aluminium alcoholates, and is preferably poor in Na and Fe. Fine-particle hydrous aluminium oxide with a particle-size spectrum of at least 95% vol.-%≤100 µm is used. These values, averaged over a plurality of crystallites, are each relative to the average diameter which is defined below as the average diameter of the primary crystallites. In detail, the hydrous aluminium oxide typically has the following particle-size spectrum:

91 vol.-%≤90 µm
51 vol.-%≤45 µm
27 vol.-%≤25 µm.

Preferably, at least 97 vol.-% of the particles of the hydrous aluminium oxide (relative to the average diameter) are smaller than or equal to 100 µm.

In principle, aqueous organic or inorganic acids with a concentration range of from 0.1% to 100%, which are diluted with water if necessary, serve as aqueous, acid-containing medium. For example, organic acids, such as acetic acid, or inorganic acids, such as nitric acid, etc. can be used to form the aqueous, acid-containing medium.

The quantity ratio between hydrous aluminium oxide and aqueous, acid-containing medium is not subject to any special limitation. Preferably, however, the aqueous, acid-containing medium is added to the hydrous aluminium oxide in such a quantity that an acid concentration of from 0.005 to 2.5 mol $H^+$/mol $Al_2O_3$, preferably 0.01 to 1.5 mol $H^+$/mol $Al_2O_3$ and in particular 0.05 to 1.0 mol $H^+$/mol $Al_2O_3$, is reached.

The H-zeolite used in the process according to the invention in step (b) can be obtained by a process which comprises the following steps:
  (i) producing aluminosilicate crystallites with an average diameter of from more than or equal to 0.01 µm to less than 0.1 µm by reacting a silicon source, an aluminium source, an alkali source and a template at a reaction temperature of more than or equal to 90° C., (ii) separating the crystallites from step (i) and optionally subjecting them to intermediate calcining,
(iii) reacting the aluminosilicate crystallites from step (ii) with an ion-exchange compound,
(iv) separating and optionally calcining the product obtained from step (iii).

In each case any of the materials usually used in the state of the art for producing aluminosilicates can be used as silicon source, aluminium source, alkali source and template. Specific examples of a suitable silicon source are for example colloidal silicic acid or alkali silicates. Examples of alkali sources are i.a. sodium hydroxide and potassium hydroxide. Examples of aluminium sources are i.a. alkali aluminates, especially sodium aluminate.

Tetraalkylammonium compounds, preferably tetrapropylammonium hydroxide (TPAOH) or tetrapropylammonium bromide (TPABr) are used as templates. Mixtures of ammonia or an organic amine and a further organic compound from the group of alcohols, preferably butanol, can also be used as templates.

If the catalyst according to a particularly preferred embodiment according to the invention is to be used in a CMO (conversion of methanol-to-olefins) or MTP (methanol-to-propylene) process, in particular a process according to DE 100 27 159 A1, the disclosure of which regarding same is hereby incorporated into the description, the proportions by weight between silicon source and aluminium source are chosen such that crystalline aluminosilicates with an Si/Al atomic ratio between approximately 50 and 250, preferably approximately 50 and 150, in particular approximately 75 and 120 are obtained.

If the finished catalyst is provided according to a further particularly preferred embodiment according to the invention for use in an OTO (olefins-to-olefins) process, in particular a process according to DE 100 00 889 A1, the disclosure of which regarding same is hereby incorporated into the description, the proportions by weight between silicon source and aluminium source are chosen such that crystalline aluminosilicates with an Si/Al atomic ratio between approximately 10 and 100, preferably between approximately 20 and 65, in particular approximately 20 and 50 are obtained.

An alkali aluminosilicate gel is produced in a manner known per se from the reaction mixture at increased temperature and optionally at increased pressure. The conversion is already possible at temperatures below 90° C. but, in this case, the reaction times are relatively long (approximately 1 week). Therefore temperatures of from 90 to 190° C., in particular from 90 to 175° C., preferably from 100 to 150° C., are preferably used, wherein at temperatures of more than 100° C. (under normal conditions) excess pressure is automatically established depending on the temperature. The aluminosilicate gel is converted to a crystalline aluminosilicate in the course of the reaction. If the temperature of the reaction mixture is higher than 190° C., the growth of the aluminosilicate primary crystallites is too rapid and primary crystallites that are too large are readily obtained, while simultaneously aluminosilicate gel is still present in the reaction mixture.

The aqueous reaction mixture preferably has a pH of from 10 to 13. At a pH of less than 10, the conversion of the aluminosilicate gel to the crystalline aluminosilicate proceeds comparatively slowly. At pH values higher than 13 the aluminosilicate crystals can in some cases dissolve again.

The formation of the crystalline aluminosilicate primary crystallites can be controlled by suitable selection of the silicon source, the aluminium source, the alkali source and the template as well as by suitable selection of the temperature and of the pH and stirring speed. However, it is essential above all that the reaction is stopped when the obtained primary crystallites have an average diameter of between 0.01 μm and less than 0.1 μm. Preferably, the average diameter of the primary crystallites is in the range of from 0.01 to 0.06 μm. Particularly good results are obtained if the average diameter of the primary crystallites is in the range of from 0.015 to 0.05 μm. If the average diameter is smaller than 0.01 μm, both the activity and the life of the catalysts are reduced considerably.

The average diameter of the primary crystallites is defined as the arithmetic average (averaged over a large number of crystallites, e.g. from 10 to 100, preferably 10 to 20, for example 14 or 15) between the largest and the smallest diameter of an individual crystallite which is determined using scanning electron microscopic examinations at a magnification of 80,000. This definition is significant in the case of crystallites with an irregular crystal habit, e.g. rod-shaped crystallites. In the case of spherical or approximately spherical crystallites the largest and the smallest diameter coincide.

The scanning electron examinations take place with a LEO Field Emission Scanning Electron Microscope (LEO Electron Microscopy Inc., USA) using powder samples of the catalyst which had previously been redispersed in acetone, treated with ultrasound for 30 seconds and then deposited on a support (Probe Current Range: 4 pA to 10 nA). Measurement takes place at 80,000 magnification. The values could be confirmed at 253,000 magnification.

To this end, several test runs are carried out. After only a few tests, the optimum parameters on the basis of which the required size ranges of the primary crystallites are reached can be ascertained. A further sign of the end of the reaction is that the pH of the reaction mixture suddenly increases.

It is not necessary for a new reaction mixture to be produced in each case. Instead, to produce the aluminosilicate gel, the silicon source, the alkali source, the aluminium source, the template and the water from the mother liquors of previous syntheses can be used and supplemented by the quantities of the named compounds required for the synthesis of the aluminosilicate gel.

The formation of the aluminosilicate primary crystallites preferably takes place at a pH between 10 and 13, wherein the reaction mixture is stirred. In this way, the size distribution of the primary crystallites is homogenized. However, the stirring speed is preferably to be no more than 900 revolutions per minute (rpm). At higher stirring speeds, the proportion of smaller primary crystallites is higher, which may be advantageous provided that it is ensured that the average diameter of all the primary crystallites is at least 0.01 μm.

The primary crystallites can sometimes be combined to form agglomerates which however are only loosely bonded to one another, such as for example in a filter cake. The primary crystallites can be relatively easily recovered from the latter, e.g. by dispersion of the filter cake in an aqueous medium and by stirring the dispersion.

The formation of such agglomerates or pre-agglomerates from primary crystallites is preferred for the subsequent separating step and can also be brought about in targeted manner by adding a flocculant to the aqueous reaction medium. In general, a cationic organic macromolecular compound is used as flocculant.

The addition of flocculant not only facilitates the separation off of the primary crystallites in the form of pre-agglomerates from the reaction medium (improved filterability), but also causes the primary crystallites combined to form pre-agglomerates to already be largely equivalent in terms of size, structure and accumulation of the primary crystallites to the agglomerates formed in the subsequent stage.

The pre-agglomerates are dried and preferably subjected to an intermediate calcining, which is first preferably carried out in an inert atmosphere at approximately 200 to 350° C., in particular at approximately 250° C., wherein one part of the template is desorbed. The intermediate calcining can then be completed in an oxidizing atmosphere at approximately 500 to 600° C., wherein any residual quantity of template still present is burnt off. In general, the pre-agglomerates are subjected to intermediate calcining for approximately 1 to 20 hours in the inert atmosphere and approximately 1 to 30 hours in the oxidizing atmosphere.

In step (ii), the product from step (i) is reacted with a proton-containing or proton-releasing substance for the exchange of the alkali ions in aqueous medium. For example, the ion exchange can be carried out with the help of a diluted mineral acid, such as e.g. hydrochloric acid or sulphuric acid, or an organic acid, such as e.g. acetic acid. The ion exchange is preferably carried out accompanied by stirring for at least an hour at temperatures between 25 and 100° C., wherein at least some of the alkali ions in the pre-agglomerates of the primary crystallites are exchanged for hydrogen ions. If necessary, the ion exchange can be repeated under the same conditions.

As an alternative to diluted acid, the ion exchange can also be carried out using an ammonium salt solution under comparable conditions. In this case, the alkali ions are exchanged for ammonium ions. If the thus-obtained product is subjected to an intermediate calcining, ammonia is removed and a product containing protons is obtained.

In step (iii) of the process, the product containing protons (H-zeolite) from step (b) is separated off (for example by filtration), dried and again subjected to drying and optionally calcining. This calcining can be carried out at temperatures of from 400 to 800° C., preferably at approximately 600° C. over a period of from 5 to 20 hours.

When the above-defined primary crystallite size is complied with, particularly good catalysts are obtained if fine-particle hydrous aluminium oxide is added in a quantity of from approximately 10 wt.-% to approximately 40 wt.-%, relative to the total weight of hydrous aluminium oxide and H-zeolite, to the H-zeolite.

By mixing the H-zeolite in step b) with the pre-mixture of fine-particle hydrous aluminium oxide and aqueous, acid-containing medium from step a), the agglomerates of aluminosilicate primary crystallites are bonded together by the fine-particle hydrous aluminium oxide. This peptization of the hydrous aluminium oxide causes the primary crystallites, or the agglomerates of the aluminosilicate, to be bonded together by the fine-particle hydrous aluminium oxide. The composites generally have dimensions of from 20 to 1000 μm, in particular from 50 to 800 μm. These values are also average dimensions which are defined as specified above.

The product from step (b) is subjected to calcining in step (c). In general, this can be carried out for 1 to 12 hours at temperatures of between approximately 500° C. and 850° C. However, within the framework of the present invention, it was also surprisingly found that the calcining is particularly advantageously carried out for 6 hours or less at a temperature in the range of from 500 to 700° C., in particular for 1 to 5 hours in the range of from 550° C. to 600° C. As a result of this comparatively short calcining at high temperatures, the acidity of the acid centres of the catalyst can clearly be advantageously influenced and the stability of the catalyst according to the invention simultaneously increased. It was also found that this advantageous "intensified" calcining also has positive effects on the catalytic properties of the aluminosilicate-based catalyst in the case of other aluminosilicate catalysts when (any) other aluminium, alkali and silicon sources, any templates as well as binders not according to the invention are used.

The thus-obtained end-product can, as mentioned above, be particularly advantageously used as catalyst in CMO or MTP and OTO processes. However, in principle, use as catalyst in other carbon conversion reactions, such as in particular olefin-to-diesel (COD) processes, dewaxing processes, alkylations, the conversion of paraffin to aromatic compounds (CPA) as well as related reactions is also not ruled out.

The present invention thus also provides a catalyst which can be obtained by the above-described process.

The construction of the catalyst from primary crystallites, agglomerates and binder particles also determines the BET surface area, measured according to DIN 66131, which is usually in the range of from 300 to 600 $m^2/g$. The pore volume, which is ascertained using the mercury porosimetry method according to DIN 66133, for the catalysts that can be obtained according to the invention is preferably in the range of from 0.31 to 0.44 $cm^3/g$, more preferably in the range of from 0.36 to 0.44 $cm^3/g$, particularly preferably in the range of from 0.38 to 0.44 $cm^3/g$ and quite particularly preferably in the range of from 0.41 to 0.44 $cm^3/g$. Preferably, at least 10%, especially at least 20%, and in particular at least 60% of the pores have a diameter of from 14 to 80 nm.

The combination of BET surface area, pore volume and pore diameter represents a particularly suitable selection for obtaining catalysts with high activity and selectivity and a long life.

The invention is explained in more detail by the non-limitative examples below.

EXAMPLES

The average primary crystallite size was ascertained as described above with the help of scanning electron examinations.

The average lateral compressive strength was determined from the force that acts on the lateral face (longest side) of the shaped bodies until they crack. For this, 50 shaped bodies with a length in the range of from 5.5 to 6.5 mm were selected from a representative sample of shaped bodies and measured individually. The shaped bodies were free of cracks and shaped straight. A shaped body was placed between two measuring jaws (one movable and one fixed). The movable measuring jaw was then moved evenly against the shaped body until the shaped body cracked. The crack value in kiloponds (kp), measured with a measuring apparatus from Schleuniger, was divided by the length of the shaped body in order to obtain the lateral compressive strength of the shaped body. The average lateral compressive strength was then determined from 50 individual measurements.

The pore volume was measured using the mercury porosimetry method and the pore diameter calculated according to DIN 66133.

The average methanol conversion rate was measured as described in application example 1 below.

Reference Example 1: Production of an H-zeolite with an Average Primary Crystallite Size of 0.03 µm A reaction mixture was produced by intimate mixing of two solutions at room temperature in a 40-liter autoclave. The two solutions were called solution A and solution B. Solution A was produced by dissolving 2218 g tetrapropylammonium bromide in 11 kg deionized water. 5000 g of a silicic acid customary in the trade was added to this solution. Solution B was produced by dissolving 766 g NaOH and then 45.6 g $NaAlO_2$ in 5.5 liters of deionized water. The still warm solution B was added to solution A. The autoclave was then closed and taken to the reaction temperature accompanied by stirring at approximately 60 rpm. The reaction was ended once the average particle diameter of the primary crystallites was 0.03 µm. After cooling, the autoclave was opened, the product removed from the reaction vessel and filtered. The filter cake was suspended in approximately 40 liters of deionized water, mixed with approximately 5 liters of a 0.4 wt.-% aqueous suspension of a flocculant customary in the trade, followed by decanting after stirring and settling of the pre-agglomerates of the solid. The described wash process was repeated until the wash water had a pH of from 7 to 8 and a Br concentration of less than 1 ppm. The suspension in which pre-agglomerates of primary crystallites were to be seen, which were clearly held together by the flocculant, was filtered. The filter cake was then dried at 120° C. for 12 hours.

The dried filter cake was reduced to a particle size of 2 mm with a granulator customary in the trade.

The granules were taken to 350° C. at a heating rate of 1° C./minute under nitrogen (1000 Nl/h) and calcined at 350° C. for 15 hours under nitrogen (1000 Nl/h). The temperature was then increased to 540° C. at a heating rate of 1° C./minute and the granules were calcined in air for 24 hours at this temperature in order to burn off the remaining tetrapropylammonium bromide.

The calcined Na zeolite was suspended in 5 times the quantity of a 1-molar aqueous HCl solution and taken to 80° C. Stirring was carried out at this temperature for an hour. Then approximately 1 liter of a 0.4 wt.-% suspension of the flocculant was added, and the supernatant acid was decanted after the solid had settled. The thus-described procedure was repeated once more. In approximately 10 wash procedures the solid was suspended each time in 60 liters of deionized water accompanied by stirring and mixed with an average of 100 ml of a 0.4 wt.-% suspension of the flocculant. After the zeolite had settled, the remaining solution was decanted. When the level of $Cl^-$ in the wash water was <5 ppm, the suspension was filtered off and dried for 15 hours at 120° C.

The dried H-zeolite was reduced to 2 mm with a granulator customary in the trade and taken to 540° C. in air at a heating rate of 1° C./minute and calcined in air for 10 hours at this temperature.

Example 1: Catalyst 1

In a kneader-mixer customary in the trade, 61 kg demineralized water and 57 kg of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 69 kg of a solution consisting of 39 kg 57.2% nitric acid and 30 kg demineralized water were added slowly to this mixture. This mixture was kneaded for 60 minutes until plasticization and homogenization occurred. 235 kg of the calcined H-zeolite from reference example 1, which was ground to a particle size of less than approximately 500 µm on a mill customary in the trade, was then added. Mixing was carried out for a further 30 minutes and another approximately 25 kg water was added to improve the consistency of the material. After mixing in 20 kg steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 1.5 kp/mm (14.7 N/mm)

Mercury pore volume: 0.31 $cm^3/g$

Average methanol conversion rate a): 95.2% a) averaged over 200-400 hours-on-stream (HOS)

Example 2: Catalyst 2

In a kneader-mixer customary in the trade, 54 kg demineralized water and 50 kg of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 60 kg of a solution consisting of 33 kg 58.2% nitric acid and 27 kg demineralized water were added slowly to this mixture. This mixture was kneaded for 60 minutes until plasticization and homogenization occurred. 200 kg of the calcined H-zeolite from reference example 1, which was ground to a particle size of less than approximately 500 µm on a mill customary in the trade, was then added. Mixing was carried out for a further 30 minutes and another approximately 18 kg water was added to improve the consistency of the material. After mixing in 17 kg steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 1.5 kp/mm (14.7 N/mm)

Mercury pore volume: 0.33 $cm^3/g$

Average methanol conversion rate a): 95.1% a) averaged over 200-400 hours-on-stream (HOS)

Example 3: Catalyst 3

In a double-Z-kneader customary in the trade, 198 g demineralized water and 145 g of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 130 g of a solution consisting of 31 g 52.2% nitric acid and 99 g demineralized water were added slowly to this mixture. This mixture was kneaded for 60 minutes until plasticization and homogenization occurred. 600 g of the calcined H-zeolite from reference example 1, which was ground to a particle size of less than approximately 500 µm on a mill customary in the trade, was then added. Mixing was carried out for a further 30 minutes and another approximately 11 g water was added to improve the consistency of the material. After mixing in 50 g steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 0.8 kp/mm (7.8 N/mm)
Mercury pore volume: 0.38 cm³/g
Average methanol conversion rate a): 97.6%
a) averaged over 200-400 hours-on-stream (HOS)

Example 4: Catalyst 4

In a double-Z-kneader customary in the trade, 104 g demineralized water and 102 g of a hydrous aluminium oxide, customary in the trade and capable of being peptized, with a particle-size spectrum of 91 vol.-%≤90 μm; 51 vol.-%≤45 μm and 27 vol.-%≤25 μm were mixed. 127 g of a solution consisting of 75 g 52.5% nitric acid and 52 g demineralized water were added slowly to this mixture. This mixture was kneaded for 60 minutes until plasticization and homogenization occurred. 400 g of the calcined H-zeolite from reference example 1, which was ground to a particle size of less than approximately 500 μm on a mill customary in the trade, was then added. Mixing was carried out for a further 30 minutes and another approximately 150 g water was added to improve the consistency of the material. After mixing in 34 g steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.
Average lateral compressive strength: 0.8 kp/mm (7.8 N/mm)
Mercury pore volume: 0.41 cm³/g
Average methanol conversion rate a): 99.1%
Average olefin selectivity a):
Propylene: 43.7%
Butenes: 21.6%
$C_{2-4}$ olefins: 72.0%
a) averaged over 200-400 hours-on-stream (HOS)

Example 5: Catalyst 5

In a double-Z-kneader customary in the trade, 25 kg demineralized water and 23 kg of a hydrous aluminium oxide, customary in the trade and capable of being peptized, with a particle-size spectrum of 91 vol.-%≤90 μm; 51 vol.-%≤45 μm and 27 vol.-%≤25 μm were mixed. 28 kg of a solution consisting of 16 kg 57.2% nitric acid and 12 kg demineralized water was added slowly to this mixture. This mixture was kneaded for 60 minutes until plasticization and homogenization occurred. 94 kg of the calcined H-zeolite from reference example 1, which was ground to a particle size of less than approximately 500 μm on a mill customary in the trade, and 2 kg hollow microspheres as burnout substance were then added. Mixing was carried out for a further 30 minutes and another approximately 10 kg water was added to improve the consistency of the material. After mixing in 8 kg steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.
Average lateral compressive strength: 0.9 kp/mm (8.8 N/mm)
Mercury pore volume: 0.44 cm³/g
Average methanol conversion rate a): 99.0%
a) averaged over 200-400 hours-on-stream (HOS)

Example 6: (Comparison Example): Catalyst 6

750 g of the calcined H-zeolite from reference example 1 was ground to a particle size of less than approximately 500 μm with the help of a laboratory mill and dry mixed in a double-Z-kneader customary in the trade with 220 g of a hydrous aluminium oxide, customary in the trade and capable of being peptized, with a particle-size spectrum of 98 vol.-%≤90 μm; 95 vol.-%≤45 μm and 55 vol.-%≤25 μm for 15 minutes. 487.5 g of a 1.5 wt.-% aqueous acetic acid solution and 50 g steatite oil were added slowly to this mixture. After adding 55 g of a 1.5 wt.-% aqueous acetic acid solution, subsequent kneading was carried out for 30 minutes and the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.
Average lateral compressive strength: 0.6 kp/mm (5.9 N/mm)
Mercury pore volume: 0.46 cm³/g
Because of the low lateral compressive strength, the average methanol conversion rate could not be measured; but it can be estimated at over 99%.

Example 7: (Comparison Example): Catalyst 7

700 g of the calcined H-zeolite from reference example 1 was ground to a particle size of less than approximately 500 μm with the help of a laboratory mill and dry mixed in a double-Z-kneader customary in the trade with 303 g of a hydrous aluminium oxide, customary in the trade and capable of being peptized, with a particle-size spectrum of 91 vol.-%≤90 μm; 51 vol.-%≤45 μm and 27 vol.-%≤25 μm and 105 g paraffin wax for 15 minutes. 245 g demineralized water and 127 g of a 25 wt.-% aqueous citric acid solution and a further 135 g demineralized water were added slowly to this mixture. After adding 56 g steatite oil, subsequent kneading was carried out for 5 minutes and the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.
Average lateral compressive strength: 0.7 kp/mm (6.9 N/mm)
Mercury pore volume: 0.47 cm³/g
Because of the low lateral compressive strength, the average methanol conversion rate could not be measured; but it can be estimated at over 99%.

Example 8: (Comparison Example): Catalyst 8

700 g of the calcined H-zeolite from reference example 1 was ground to a particle size of less than approximately 500 μm with the help of a laboratory mill and dry mixed in a double-Z-kneader customary in the trade with 302 g of a hydrous aluminium oxide, customary in the trade and capable of being peptized, with a particle-size spectrum of 91 vol.-%≤90 μm; 51 vol.-%≤45 μm and 27 vol.-%≤25 μm and 136 g paraffin wax for 15 minutes. 245 g demineralized water and 127 g of a 25 wt.-% aqueous citric acid solution and a further 206 g demineralized water were added slowly to this mixture. After adding 56 g steatite oil, subsequent kneading was carried out for 5 minutes and the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 0.4 kp/mm (3.9 N/mm)

Mercury pore volume: 0.51 cm$^3$/g

Because of the low lateral compressive strength, the average methanol conversion rate could not be measured; but it can be estimated at over 99%.

Example 9: (Comparison Example): Catalyst 9

750 g of the calcined H-zeolite from reference example 1 was ground to a particle size of less than approximately 500 µm with the help of a laboratory mill and dry mixed in a double-Z-kneader customary in the trade with 225 g of a hydrous aluminium oxide, customary in the trade and capable of being peptized, with a particle-size spectrum of 91 vol.-%≤90 µm; 51 vol.-%≤45 µm and 27 vol.-%≤25 µm for 15 minutes. 583 g of a 1.5 wt.-% aqueous nitric acid solution and 50 g steatite oil were added slowly to this mixture. Subsequent kneading was carried out for 30 minutes and the plasticized material was extruded in an extruder customary in the trade to form shaped bodies with a diameter of approximately 3 mm and a length of approximately 6 mm. The shaped bodies were then dried for 16 hours at 120° C. and calcined for 5 hours at 600° C.

Average lateral compressive strength: 2.0 kp/mm (19.5 N/mm)

Mercury pore volume: 0.32 cm$^3$/g

Example 10: Catalyst 10

In a double-Z-kneader customary in the trade, 175 g demineralized water and 170 g of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 199 g of a solution consisting of 64 g 99-100% acetic acid and 135 g demineralized water were added slowly to this mixture. This mixture was kneaded for 60 minutes until plasticization and homogenization occurred. 700 g of the calcined H-zeolite from reference example 1, which was ground to a particle size of less than approximately 500 µm on a mill customary in the trade, was then added. Mixing was carried out for a further 30 minutes and another approximately 80 g water was added to improve the consistency of the material. After mixing in 59 g steatite oil and mixing for 10 minutes, the plasticized material was extruded in an extruder customary in the trade to form shaped bodies with a diameter of approximately 3 mm and a length of approximately 6 mm. The shaped bodies were then dried for 16 hours at 120° C. and calcined for 5 hours at 600° C.

Average lateral compressive strength: 0.90 kp/mm (8.8 N/mm)

Mercury pore volume: 0.36 cm$^3$/g

Example 11: Catalyst 11

In a kneader-mixer customary in the trade, 910 g demineralized water and 889 g of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 1108 g of a solution consisting of 653 g 52.5% nitric acid and 455 g demineralized water were added slowly to this mixture. This mixture was kneaded for 60 minutes until plasticization and homogenization occurred. 3000 g of the calcined H-zeolite from reference example 1, which was ground to a particle size of less than approximately 500 µm on a mill customary in the trade, was then added. Mixing was carried out for a further 30 minutes and another approximately 350 g water was added to improve the consistency of the material. After mixing in 252 g steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 1.3 kp/mm (12.7 N/mm)

Mercury pore volume: 0.36 cm$^3$/g

Average methanol conversion rate a): 97.2%

Average olefin selectivity a):

Propylene: 43.2%

Butenes: 20.3%

$C_{2-4}$ olefins: 70.0% a) averaged over 200-400 hours-on-stream (HOS)

Example 12: Catalyst 12

In a kneader-mixer customary in the trade, 1869 g demineralized water and 1827 g of a hydrous aluminium oxide, customary in the trade and capable of being peptized, with a particle-size spectrum of 91 vol.-%≤90 µm; 51 vol.-%≤45 µm and 27 vol.-%≤25 µm were mixed. 2276 g of a solution consisting of 1342 g 52.5% nitric acid and 934 g demineralized water were added slowly to this mixture. This mixture was kneaded for 60 minutes until plasticization and homogenization occurred. 3000 g of the calcined H-zeolite from reference example 1, which was ground to a particle size of less than approximately 500 µm on a mill customary in the trade, was then added to 2986 g of the plasticized material obtained. Mixing was carried out for a further 30 minutes and another approximately 200 g water was added to improve the consistency of the material. After mixing in 252 g steatite oil and mixing for 10 minutes, the plasticized material was extruded in an extruder customary in the trade to form shaped bodies with a diameter of approximately 3 mm and a length of approximately 5 mm. The shaped bodies were then dried for 16 hours at 120° C. and calcined for 5 hours at 600° C.

Average lateral compressive strength: 1.4 kp/mm (13.7 N/mm)

Mercury pore volume: 0.31 cm$^3$/g

Average methanol conversion rate a): 96.1%

Average olefin selectivity a):

Propylene: 42.2%

Butenes: 19.4%

$C_{2-4}$ olefins: 68.3% a) averaged over 200-400 hours-on-stream (HOS)

Application Example 1

This application example shows the advantages of the catalyst according to the invention using catalytic data of the CMO process (conversion of methanol to olefins process) in an isothermal fixed-bed reactor.

All catalysts tested were treated for 48 hours with steam before the methanol/water mixture was released. The methanol/water feed was then passed over the CMO catalyst in an isothermal fixed-bed reactor with a WHSV of 3 (kg/(kg·h), i.e. three kilograms total feed per kilogram of catalyst and per hour at a pressure of 1 bar for the conversion of methanol. The methanol contents of the gas phase and of the liquid phase at the outlet of the CMO catalyst reactor were determined with gas-chromatography analysis processes. Table 1 shows the catalytic properties of the examined catalysts in the isothermal reactor under the following conditions: $T^R_{OUT}$ (temperature of the reactor at the outlet) =450° C.; load: WHSV=1 h$^{-1}$ (kg methanol/kg catalyst and hour), weight ratio (MeOH:H$_2$O)=1:2, for 200-400 HOS (hours-on-stream).

When the catalytic properties are compared (Table 1), it becomes clear that the catalysts according to the invention have a high MeOH conversion rate with, at the same time, a high average lateral compressive strength. Although catalyst 6, which corresponds to the catalyst of Example 1 of EP 1 424 128, has a high MeOH conversion rate, it has a lateral compressive strength which, at 0.6 kp/mm, lies below the threshold of 0.8 kp/mm as the acceptable minimum lateral compressive strength. The catalysts 7 and 8 also have unacceptable lateral compressive strengths. The average methanol conversion rate was not determined here, in order to avoid a clogging of the reactor by a catalyst that is breaking up.

TABLE 1

| Catalyst | Pore volume [cm$^3$/g] | Average MeOH conversion rate (200-400 HOS) [%] | Average lateral compressive strength [kp/mm] |
|---|---|---|---|
| 1 | 0.31 | 95.2 | 1.5 |
| 2 | 0.33 | 95.1 | 1.5 |
| 3 | 0.38 | 97.6 | 0.8 |
| 4 | 0.41 | 99.1 | 0.8 |
| 5 | 0.44 | 99.0 | 0.9 |
| 6 (comparison) | 0.46 | >99*[1] | 0.6 |
| 7 (comparison) | 0.47 | >99*[1] | 0.7 |
| 8 (comparison) | 0.51 | >99*[1] | 0.4 |

*[1]: estimated

Application Example 2

This application example serves to determine the selectivity of the catalysts according to the invention in the CMO process.

The catalysts were pre-treated and tested in the same way as described in application example 1. The compositions of the gas phase and of the liquid phase at the outlet of the CMO catalyst reactor were determined with gas-chromatography analysis processes.

The selectivity $S_i$ results from the molar carbon content of component i relative to the converted carbon:

$$S_i = \frac{\dot{n}_{i\,out} \cdot \varepsilon_i^C}{\dot{n}_{MeOH\,in} \cdot \varepsilon_{MeOH}^C - \dot{n}_{MeOH\,out} \cdot \varepsilon_{MeOH}^C}$$

In order to rule out the influence of the carbon balance, the selectivity was normalized to 100% as follows:

$$\overline{S}_i = 100\% * \frac{\dot{n}_{i\,out} \cdot \varepsilon_i^C}{\sum_{i}^{i=N} \dot{n}_{i\,out} \cdot \varepsilon_i^C}$$

For this calculation, dimethyl ether was not taken into account as product.

$S_i$: selectivity of component i $\overline{S}_i$: normalized selectivity of component i $\varepsilon_i^C$: number of carbon atoms of component $\dot{n}_i$: molar flux of component i Table 2 shows the methanol conversion rate and the olefin selectivity of the examined catalysts in the isothermal reactor under the same conditions as described in application example 1.

TABLE 2

| Catalyst | Pore volume [cm$^3$/g] | Average MeOH conversion rate (200-400 HOS) [%] | Average lateral compressive strength [kp/mm] | Average olefin selectivity | | |
|---|---|---|---|---|---|---|
| | | | | Propylene (200-400 HOS) [%] | Butylenes (200-400 HOS) [%] | C$_{2-4}$ olefins (200-400 HOS) [%] |
| 4 | 0.41 | 99.1 | 0.8 | 43.7 | 21.6 | 72.0 |
| 11 | 0.36 | 97.2 | 1.3 | 43.2 | 20.3 | 70.0 |
| 12 | 0.31 | 96.1 | 1.4 | 42.2 | 19.4 | 68.3 |

The catalysts can be regenerated after a first cycle ends by first stopping the MeOH stream. Nitrogen is then fed in to expel the remaining MeOH. Finally, oxygen is slowly added to the nitrogen in gradually increasing concentrations in order to burn off the hydrocarbon deposited on the catalysts. The temperature of the catalysts is usually kept below 480° C. The regeneration of the catalysts is ended when the oxygen content of the nitrogen stream is the same at the inlet and at the outlet of the catalyst bed.

When the catalytic properties of Table 2 are compared, it becomes clear that all catalysts 4, 11 and 12 according to the invention have high average olefin selectivities.

Catalyst 4, which has the largest pore volume, displays the best catalytic performance.

The invention claimed is:

1. A process for producing a catalyst comprising a pentasil-type crystalline aluminosilicate, comprising the steps of:

(a) treating hydrous aluminium oxide with an aqueous, acid-containing medium to provide a plasticized and homogenous mixture,
(b) mixing the plasticized and homogenous mixture hydrous aluminium oxide treated with the aqueous, acid-containing medium from step (a) with a pentasil-type H-zeolite with an average diameter of its primary crystallites being 0.01 µm and 0.1 µm to form a mixture, and
(c) calcining the mixture obtained in step (b),
wherein at least 95 vol.-% of the particles of hydrous aluminium oxide, relative to an average diameter, are smaller than or equal to 100 µm, and
wherein the catalyst has a pore volume of 0.31 to 0.44 cm$^3$/g and an average lateral compressive strength of 0.8 to 1.5 kp/mm (7.8 to 14.7 N/mm).

2. The process according to claim 1, wherein the aqueous, acid-containing medium comprises an aqueous inorganic acid.

3. The process according to claim 1, wherein the acid-containing medium comprises an aqueous organic acid.

4. The process according to claim 1, wherein in step (a) the aqueous, acid-containing medium is added to the hydrous aluminium oxide in a quantity such that an acid concentration of from 0.005 to 2.5 mol H$^+$/mol Al$_2$O$_3$ results.

5. The process according to claim 1, where at least 97 vol.-% of the particles of the hydrous aluminium oxide (relative to the average diameter) are smaller than or equal to 100 µm.

6. The process according to claim 1, wherein the hydrous aluminum oxide particles have a particle-size spectrum of
91 vol.-%≤90 µm
51 vol.-%≤45 µm, and
91 vol.-%≤90 µm,
in each case relative to the average particle diameter.

7. The process according to claim 1, wherein the hydrous aluminium oxide is present in a quantity of from 10 wt.-% to 40 wt.-% aluminium oxide, relative to the total weight of the product.

8. The process according to claim 1, wherein the calcining takes place at a temperature in the range of from 500 to 700° C. for 6 hours or less.

9. The process according to claim 1, wherein the pentasil-type H-zeolite is obtained by a process comprising the following steps:
(i) producing aluminosilicate crystallites with an average diameter of from more than or equal to 0.01 µm to less than 0.1 µm by reacting a silicon source, an aluminium source, an alkali source and a template at a reaction temperature of more than or equal to 90° C.,
(ii) separating the crystallites from step (i),
(iii) reacting the aluminosilicate crystallites from step (ii) with an ion-exchange compound,
(iv) separating and calcining the product obtained from step (iii).

10. The process of claim 1 wherein the acid-containing medium is selected from the group consisting of sulfuric acid and nitric acid.

11. The process of claim 1, wherein the acid-containing medium is selected from the group consisting of acetic acid, citric acid, formic acid and oxalic acid.

12. The process of claim 1 wherein in step (a) the aqueous, acid-containing medium is added to the hydrous aluminium oxide in a quantity such that an acid concentration of from 0.01 to 1.5 mol H$^+$/mol Al$_2$O$_3$ results.

13. The catalyst of claim 1, the pore volume of which, determined using mercury porisometry, is 0.41 to 0.44 cm$^3$/g.

14. The process of claim 1 wherein in step (a) the aqueous, acid-containing medium is added to the hydrous aluminium oxide in a quantity such that an acid concentration of from 0.05 to 1.0 mol H$^+$/mol Al$_2$O$_3$ results.

* * * * *